(12) United States Patent
Gogolewski

(10) Patent No.: US 8,211,351 B2
(45) Date of Patent: Jul. 3, 2012

(54) RESORBABLE POLYMERIC MEDICAL GOODS WITH IMPROVED MECHANICAL PROPERTIES AND METHOD FOR PRODUCING SAME

(75) Inventor: Sylwester Gogolewski, Davos Platz (CH)

(73) Assignee: Synthes USA, LLC, West Chester, PA (US)

( * ) Notice: Subject to any disclaimer, the term of this patent is extended or adjusted under 35 U.S.C. 154(b) by 1041 days.

(21) Appl. No.: 11/568,954

(22) PCT Filed: May 13, 2004
(Under 37 CFR 1.47)

(86) PCT No.: PCT/CH2004/000290
§ 371 (c)(1),
(2), (4) Date: Jun. 27, 2008

(87) PCT Pub. No.: WO2005/110506
PCT Pub. Date: Nov. 24, 2005

(65) Prior Publication Data
US 2009/0030415 A1    Jan. 29, 2009

(51) Int. Cl.
*B29C 71/00* (2006.01)
(52) U.S. Cl. .................... 264/343; 264/323
(58) Field of Classification Search ............ 264/211, 264/288.4, 289.3, 343, 300, 323
See application file for complete search history.

(56) References Cited

U.S. PATENT DOCUMENTS

| | | | |
|---|---|---|---|
| 5,484,565 A * | 1/1996 | Larsen et al. | 264/230 |
| 5,492,697 A * | 2/1996 | Boyan et al. | 623/16.11 |
| 5,728,336 A | 3/1998 | Gogolewski et al. | |
| 6,383,190 B1 | 5/2002 | Preissman | |
| 6,495,631 B1 * | 12/2002 | Randall et al. | 525/186 |

(Continued)

FOREIGN PATENT DOCUMENTS
EP     0 499 917 A1     8/1992
(Continued)

OTHER PUBLICATIONS

Weiler W. et al., "Enhancement of the mechanical properties of polylactides by solid-state extrusion." Biomaterials. Mar. 1996;17(5):529-35.

(Continued)

*Primary Examiner* — Christina Johnson
*Assistant Examiner* — Galen Hauth
(74) *Attorney, Agent, or Firm* — Woodcock Washburn LLP

(57) ABSTRACT

The method for producing resorbable or degradable polymeric medical devices by applying compressive forces on solid polymeric objects containing liquid or solid additives, is characterized in that: A) the additives are able to promote the slip-page of the polymeric objects through the forming device, facilitate transient chain mobility and promote chain orientation; B) said additives are present in an amount of 0.005 to 20% of the dry weight of said polymeric objects; C) the solubility parameters of said additives being selected in such a way that after absorbing by said polymeric objects the additives do not dissolve more than 0.01 to 1% of the total mass of said polymeric objects; D) said applying of compressive forces is performed minimally at a temperature of $T_{min}=T_g-50°$ C., $T_g$ being the glass transition temperature of the polymer the said object is made of polymer; and E) said applying of compressive forces is performed maximally at a temperature $T_{max}=T_m-5°$ C., $T_m$ being the melting peak temperature of the polymer the said object is made of said polymer objects.

19 Claims, 3 Drawing Sheets

U.S. PATENT DOCUMENTS

2003/0083745 A1*   5/2003   Pohjonen et al. .......... 623/11.11

FOREIGN PATENT DOCUMENTS

| EP | 0 520 177 A1 | 12/1992 |
|---|---|---|
| JP | 03-085179 | 4/1991 |
| JP | 04-221538 | 8/1992 |
| JP | 07-313586 | 12/1995 |
| JP | 08-024347 | 1/1996 |
| JP | 09-201330 | 8/1997 |
| WO | WO-01/32100 A2 | 5/2001 |
| WO | WO 03/064531 A1 | 8/2003 |

OTHER PUBLICATIONS

International Search Report for International Application No. PCT/CH2004/000290.

"European Patent Application No. 04750971.6, Communication mailed Jun. 12, 2008", 5 pgs.

"International Patent Application Serial No. PCT/CH2004/000290, Written Opinion mailed Feb. 21, 2005", 6 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999), 7370-7379.

Tunc, D. C., "Body-absorbable osteosynthesis devices", *Clinical Materials*, 8(1-2), (1991), 119-123.

\* cited by examiner

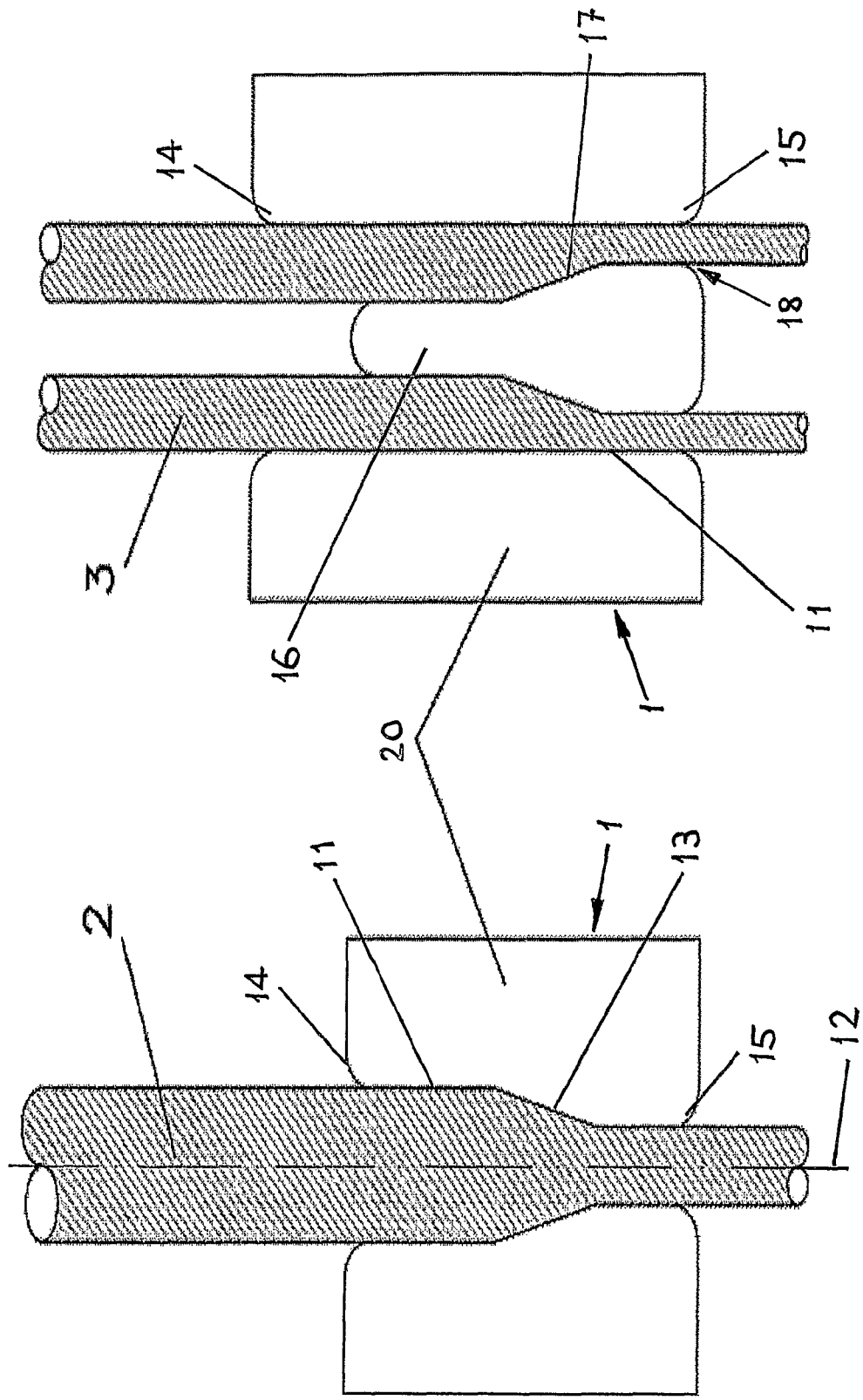

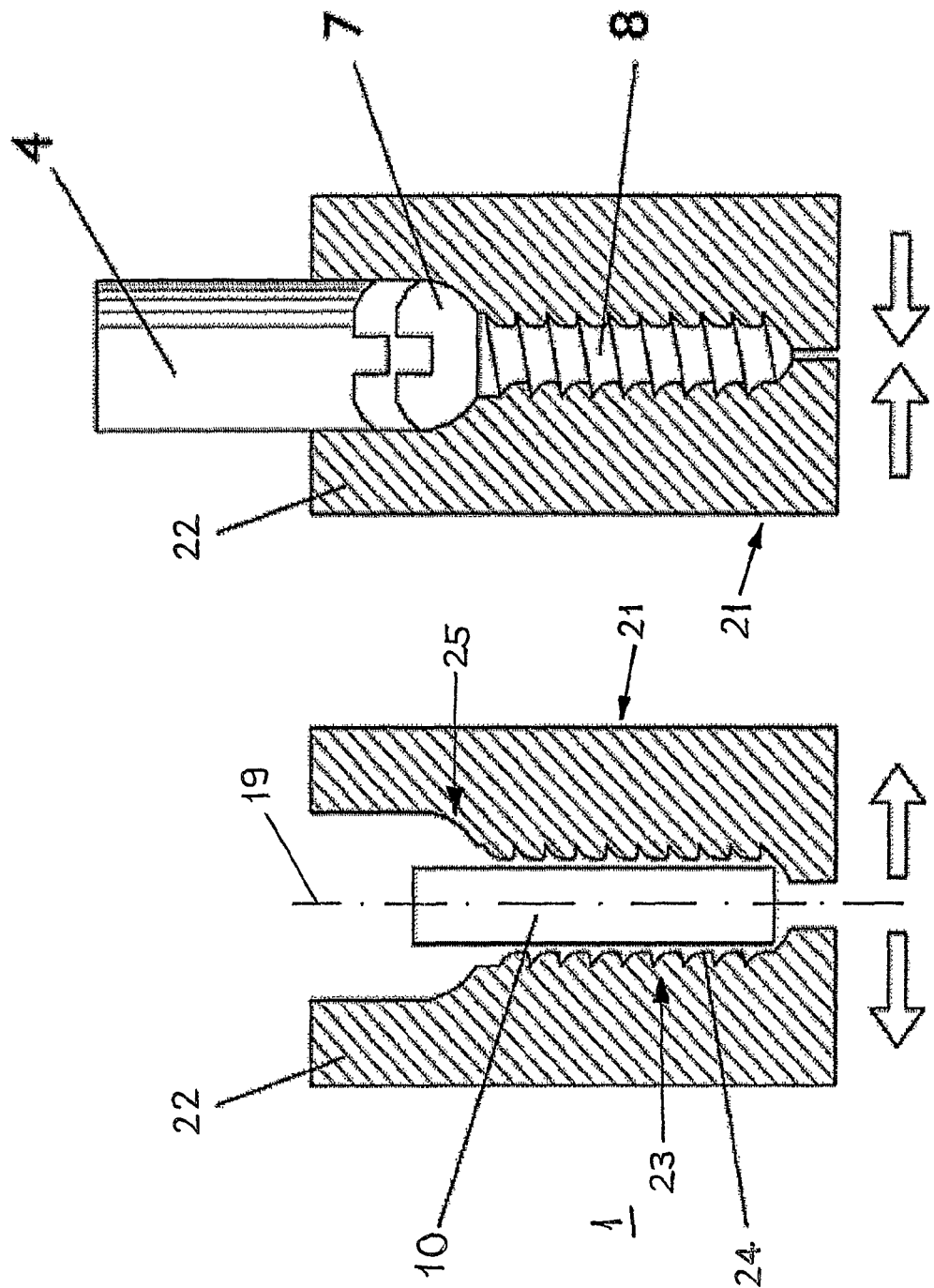

RESORBABLE POLYMERIC MEDICAL GOODS WITH IMPROVED MECHANICAL PROPERTIES AND METHOD FOR PRODUCING SAME

This invention relates to a method for producing resorbable or degradable polymeric medical devices according to the preamble of claim 1.

Bioresorbable and/or biodegradable implantable polymeric objects/devices of the invention are produced from biocompatible, bioresorbable-biodegradable polymers in their pure form, their composites with biocompatible, preferably nanosize ceramics, and their blends with thermotropic main-chain and/or side-chain liquid-crystalline polymers and/or liquid-crystalline low molecular weight compounds.

Biocompatible, bioresorbable-biodegradable polymers used in the objects/devices of the invention are from the group of polyhydroxyacids, polyurethanes, polyaminoacids, polyanhydrides, polyorthoesters, polycarbonates, polyfumarates, polyesteramides, polycaprolactones, their compounds and physical mixtures of these polymers to mention but a few.

In vivo functionality and of bioresorbable implantable polymeric objects/devices are directly related to their mechanical properties.

The mechanical properties of such objects/devices are affected by the polymer molecular weight and polydispersity, the presence in the material of reinforcing structures, e.g. liquid crystalline additives, the presence of impurities, the ability of the polymer to form the liquid crystalline structure, and last but not least by the chain orientation and overall crystallinity.

In general, the presence of impurities, flaws and voids in the bioresorbable implantable device decreases its mechanical properties, while the increase of polymer molecular weight and decrease of polydispersity, the presence of reinforcing structures, the ability to form the liquid crystalline structure and the increase in chain orientation and crystallinity, enhance the mechanical properties.

Chain orientation in polymers can be achieved by standard techniques such as cold-drawing at temperatures close to room temperatures and/or hot-drawing at elevated temperatures, i.e. temperatures above the glass transition temperature and below the melting temperature of the given polymer, calendering, rotational compression-moulding, injection-moulding at high shear rates, injection-blow moulding, blowing, extrusion at high shear rates or stirring-induced crystallization.

In general, highest draw ratios lead to polymeric objects with highest degrees of chain orientation and highest strength and moduli. These are usually achieved at temperatures close to the atmospheric melting peak temperature.

During drawing at elevated temperatures the polymeric object to be oriented is usually passed through a heated zone filled with air or flushed with inert gases (argon, nitrogen). In some cases, one of the surfaces of the polymeric object may contact the heating element (e.g. knife/pin in fiber drawing processes), while the other surface is in direct contact with the surrounding atmosphere. This results in a temperature gradient across the polymeric element, leading, to formation of defects in the oriented structure especially in the objects with large cross-sections.

The hot-drawing process usually causes undesired thermo-mechanical-oxidative degradation of the drawn polymer, the effect being especially evident for bioresorbable/biodegradable polymers which due to their chemical structure are prone to degradation.

Metallic internal fixation devices are mainly used to fix bone fractures. Among primary factors which affect performance of such devices in vivo are mechanical compatibility with bone and resistance to chemical and fretting corrosion. Too large differences in modulus between bone and may lead to high concentration of stresses at the attachment sites and to implant and/or tissue failure. Yet another problem can be the reduction of the blood supply to the implantation site leading to bone resorption and remodeling of the bone segment and implant corrosion accompanied by the release of ions and debris, which may cause toxic and/or inflammatory responses. An essential drawback results from a necessity of implant removal, especially critical in articulation (osteochondral defects) and maxillofacial surgery. For these reasons interest in using bioresorbable polymeric implants or bioresorbable implants based on polymer-ceramic composites for the fixation of bone fractures is increasing.

However, one of the limitations on the wide use of bioresorbable implants in orthopedic and trauma surgery results from the fact that mechanical properties of implants produced by common techniques involving melt-processing, such as injection-moulding, melt-extrusion or compression-moulding are far from optimal.

The techniques, which can lead to bioresorbable polymeric implants with enhanced mechanical properties, include the so-called solvent-welding process (U.S. Pat. No. 5,728,336), where melt-processes or gel-processed polymeric objects are cold-drawn or hot-drawn into highly fibrillated structures and bound together into high-strength, high-modulus implantable devices using solvents.

Other techniques include so-called "orientrusion" (Tunc DC, Body-absorbable osteosynthesis devices, Clinical Materials 8, 119(1991)]) and compression moulding of resorbable polymeric fibers of one polymer embedded in the resorbable matrix of another resorbable polymer or embedded in the resorbable matrix of the same polymer. The drawback of the latter two approaches is delamination of implants in an aqueous environment, e.g. in body fluids.

Yet, another approach to produce high-strength, high-modulus polymeric objects with a high degree of chain orientation (fibrillation) utilizes techniques used in processing of metals. These techniques, involving ram (piston-cylinder) extrusion, hydrostatic extrusion or die drawing were successfully applied to non-resorbable commodity polymers (9-13). The increased strengths and moduli of the drawn semicrystalline polymers results from transformation of the folded-chain spherulitic structure into chain-extended or at least partially extended fibrillar structure.

Die-drawing was also applied to bioresorbable polymers leading to implants with enhanced mechanical properties.

The solid-state extrusion techniques applied at present to bioresorbable polymers, and primarily to polyhydroxyacids, requires that polymer billets used for drawing are dry, contain the lowest achievable amount of residual monomers, oligomers fraction and residual polymerization and processing media. The use of dry, highly-purified billets diminishes material degradation upon solid-state extrusion. On the other hand, this makes the drawing process more difficult due to the absence of plasticizing component enhancing the slippage and alignment of chain molecules upon drawing.

On this point, the invention intends to provide remedial measures. The invention is based on the objective of providing a method for producing resorbable or degradable polymeric medical devices in which slippage of the polymeric objects through the forming device is promoted, transient chain mobility facilitated and chain orientation promoted.

The invention solves the posed problem with a method that displays the features of claim 1 as well as with a resorbable or degradable polymeric medical device manufactured according to said method and that displays the features of claim 16

The inventive method is applicable to solid, bioresorbable polymeric medical objects/devices of various geometrical shapes, initially having circular, triangular, square, rectangular or other cross-sections. Such objects in the form of pins, pegs, plates, screws, medullary nails, ribbons, monofilaments, etc., can, although they need not, be used for internal fixation of bone fractures.

The principle of the inventive method relates to pulling and/or pushing of highly-purified solid polymeric objects containing a predetermined amount of specific plasticizing liquid or solid additives through a forming device allowing elongation of the objects in direction of the pulling/pushing. These liquid or solid additives are deliberately introduced into material during the initial pre-swelling process, and their presence in bioresorbable polymeric objects enhances chain orientation due to the transient breakage of hydrogen bonding between polymer chains and undisturbed passage of the object through the forming device.

The pre-swelling process can also be applied to produce high-strength, high-modulus bioresorbable polymeric implants with complex shapes such as screws for example, by forging. In this case, the surface of high-strength, high modulus elements with fibrillated structure produced using the pulling/pushing process of this invention is swollen in adequate liquids. As a result, the polymer chains at the surface layer refold (recoil). Next, the swollen bar with a predetermined length is placed in the cavity of an open mould having a negative pattern of the required screw thread. The mould is closed and the thread is stamped into the swollen surface of the polymeric element. After this stage is completed, a piston with one end having an adequate shape for making a screw head (Phillips pin-head, socket pin-head, etc.) is inserted in the mould and pressed down to complete the screw production phase. The trace residue of liquids, which might be contained in the polymeric object, is removed through the vents in the mould by applying vacuum, at temperatures close to the glass transition temperature of the polymer.

The refolded polymer chains in the head zone of the screws produced according to the technique disclosed in this invention allow for higher plastic deformation of the polymeric object upon applying a torque to the screw, i.e. protect against a premature shearing off the screw head. The refolded polymer chains in the in the screw thread zone reduce propagation of cracks which may form upon forging.

Additives to be used for the pretreatment of solid polymeric objects are individual liquids or solids and/or mixtures of various liquids/solids. They can be nonpolar compounds as well as polar, hydrogen-bonding compounds, i.e. compounds able to form transient hydrogen bonds with the polymer. They can also be liquid-crystalline solvents and/or their mixtures with other solid or liquid additives and metal-containing liquids. Additives to be used for the pretreatment of solid polymeric objects are individual liquids or solids and/or mixtures of various liquids/solids. They can be nonpolar compounds able to destroy the network of secondary bonds existing in the polymeric objects as well as polar, hydrogen-bonding compounds, i.e. compounds able to form transient hydrogen bonds with the polymer. They can also be liquid-crystalline solvents and/or their mixtures with other solid or liquid additives and metal-containing liquids, which enhance chain orientation and/or reinforce the polymer matrix of the objects by forming of a liquid-crystalline structure.

Solubility parameters $\delta$ of the additive should be selected in such a way that the additive cannot dissolve more than 0.005 to 1 wt-% of the polymer used and preferably not more than 0.01 to 0.1% of the polymer used. Solubility parameters also called Hildebrand solubility parameters can be found in various Handbooks. They indicate the solvency behavior of a specific solvent (liquid or solid). Below are listed some examples of Hildebrand Solubility Parameters:

Hildebrand Solubility Parameters
Standard Hildebrand values from Hansen, Journal of Paint Technology Vol. 39, No. 505, February 1967 SI Hildebrand values from Barton, Handbook of Solubility Parameters, CRC Press, 1983 Values in parenthesis from Crowley, et al., Journal of Paint Technology Vol. 38, No. 496, May 1966

| Solvent | $\delta$ | $\delta$ (SI) |
| --- | --- | --- |
| n-Pentane | (7.0) | 14.4 |
| n-Hexane | 7.24 | 14.9 |
| Freon ® TF | 7.25 | |
| n-Heptane | (7.4) | 15.3 |
| Diethyl ether | 7.62 | 15.4 |
| 1,1,1 Trichloroethane | 8.57 | 15.8 |
| n-Dodecane | | 16.0 |
| White spirit | | 16.1 |
| Turpentine | | 16.6 |
| Cyclohexane | 8.18 | 16.8 |
| Amyl acetate | (8.5) | 17.1 |
| Carbon tetrachloride | 8.65 | 18.0 |
| Xylene | 8.85 | 18.2 |
| Ethyl acetate | 9.10 | 18.2 |
| Toluene | 8.91 | 18.3 |
| Tetrahydrofuran | 9.52 | 18.5 |
| Benzene | 9.15 | 18.7 |
| Chloroform | 9.21 | 18.7 |
| Trichloroethylene | 9.28 | 18.7 |
| Cellosolve ® acetate | 9.60 | 19.1 |
| Methyl ethyl ketone | 9.27 | 19.3 |
| Acetone | 9.77 | 19.7 |
| Diacetone alcohol | 10.18 | 20.0 |
| Ethylene dichloride | 9.76 | 20.2 |
| Methylene chloride | 9.93 | 20.2 |
| Butyl Cellosolve ® | 10.24 | 20.2 |
| Pyridine | 10.61 | 21.7 |
| Cellosolve ® | 11.88 | 21.9 |
| Morpholine | 10.52 | 22.1 |
| Dimethylformamide | 12.14 | 24.7 |
| n-Propyl alcohol | 11.97 | 24.9 |
| Ethyl alcohol | 12.92 | 26.2 |
| Dimethyl sulphoxide | 12.93 | 26.4 |
| n-Butyl alcohol | 11.30 | 28.7 |
| Methyl alcohol | 14.28 | 29.7 |
| Propylene glycol | 14.80 | 30.7 |
| Ethylene glycol | 16.30 | 34.9 |
| Glycerol | 21.10 | 36.2 |
| Water | 23.5 | 48.0 |

In 1936 Joel H. Hildebrand (who laid the foundation for solubility theory in his classic work on the solubility of non-electrolytes in 1916) proposed the square root of the cohesive energy density as a numerical value indicating the solvency behavior of a specific solvent.

$$\partial = \sqrt{c} = \left[\frac{\Delta H - RT}{V_m}\right]^{1/2}$$

It was not until the third edition of his book in 1950 that the term "solubility parameter" was proposed for this value and the quantity represented by a delta ($\delta$). Subsequent authors have proposed that the term "hildebrands" be adopted for solubility parameter units, in order to recognize the tremendous contribution that Dr. Hildebrand has made to solubility theory.

The table lists several solvents in order of increasing Hildebrand parameter. Values are shown in both the common form which is derived from cohesive energy densities in calories/cc, and a newer form which, conforming to standard international units (SI units), is derived from cohesive pressures. The SI unit for expressing pressure is the pascal, and SI Hildebrand solubility parameters are expressed in mega-pascals (1 mega-pascal or mpa=1 million pascals). Conveniently, SI parameters are about twice the value of standard parameters:

$$\delta/cal^{1/2}cm^{-3/2}=0.48888\times\delta/MPa^{1/2}$$

$$\delta/MPa^{1/2}=2.0455\times\delta/cal^{1/2}cm^{-3/2}$$

Literature published prior to 1984 should contain only the common form, designated $\delta$, and it is hoped that where the newer SI units are used, they are designated as such, namely $\delta/MPa^{1/2}$ or $\delta(SI)$. Obviously, one must be careful to determine which system of measurement is being used, since both forms are called Hildebrand parameters. This paper will primarily use the SI values, and the use of standard values will be noted.

It is readily apparent from the above table that by ranking solvents according to solubility parameter a solvent "spectrum" is obtained, with solvents occupying positions in proximity to other solvents of comparable "strength". If, for example, acetone dissolves a particular material, then one might expect the material to be soluble in neighboring solvents, like diacetone alcohol or methyl ethyl ketone, since these solvents have similar internal energies. It may not be possible to achieve solutions in solvents further from acetone on the chart, such as ethyl alcohol or cyclohexane—liquids with internal energies very different from acetone. Theoretically, there will be a contiguous group of solvents that will dissolve a particular material, while the rest of the solvents in the spectrum will not. Some materials will dissolve in a large range of solvents, while other might be soluble in only a few. A material that cannot be dissolved at all, such as a crosslinked three-dimensional polymer, would exhibit swelling behavior in precisely the same way.

| Solubility parameters of some polymers | |
| --- | --- |
| Polymer | $\delta/MPa^{1/2}$ |
| Poly(isobutylene) | 16.2 |
| Poly(methylmethacrylate) | 18.6 |
| Poly(vinyl acetate) | 19.2 |
| Poly(hexamethylene adipamide) | 27.8 |
| Poly(tetrafluoroethylene) | 6.2 |
| Poly(ethylene) | 7.9 |
| Poly(styrene) | 9.1 |
| Poly(vinyl chloride) | 9.7 |
| Poly(vinylidene chloride) | 12.2 |
| Poly(ethylene terephthalate) | 10.7 |
| Poly(hexemethylene adipamide) | 13.6 |

In general, the forming device should have a conical cross-section in the direction parallel to the direction of object travel. The angles of the cone should be in the range of 5 to 80° and preferably in the range of 10 to 20°.

The cross-section of the device in the direction perpendicular to the direction of object travel can be circular, ellipsoidal, square, rectangular, triangular, etc. The cross-section of the device can be solid and/or hollow, e.g. in the case when a polymer tubes are passed through the device.

When passing through the opening in the forming device, the total outer surface of the polymeric object has to be in direct contact with the device wall and/or with the device wall via a thin intermediary layer of the swelling agent squeezed out from the polymer.

Pushing and/or pulling of the polymeric object through the forming device, results in the alignment of polymer chains in the direction of travel and thus, leads to materials with higher values of tensile/flexural strength and moduli.

The type of polymers which are preferred in the invention are from the group of polyhydroxyacids: poly(L-lactide), poly(D-lactide), racemic poly(DL-lactide), poly(D/L-lactide), poly(L/DL-lactide), terpolymers of lactides, glycolide and caprolactones, copolymers of lactides and/or glycolide and trimethylene carbonate, polyurethanes, polyaminoacids, polyanhydrides, polyorthoesters, polycarbonates, polyfumarates, polyesteramides, polycaprolactones, copolymers of hydroxyacids with ethylene oxide, polyurethanes and similar. The polymers to be used in the invention can also be physical mixtures of these polymers in various proportions.

The various features of novelty which characterizes the invention are pointed out with particularity in the claims annexed to and forming part of this disclosure. For the better understanding of the invention, its operating advantages and specific objects attained by its use, reference should be had to accompanying drawings, examples and descriptive matter in which are illustrated and described preferred embodiments of the invention.

IN THE DRAWINGS

FIG. 1 shows a section through the forming device of an apparatus for preparation of continuous polymeric medical devices according to the invention.

FIG. 2 shows a section of a modified forming device;

FIG. 3a shows a section through a device allowing preparation of individual polymeric medical objects with complex shapes by forging with opened compression moulds;

FIG. 3b shows a section through a device allowing preparation of individual polymeric medical objects with complex shapes by forging with closed compression moulds.

Figure 4:
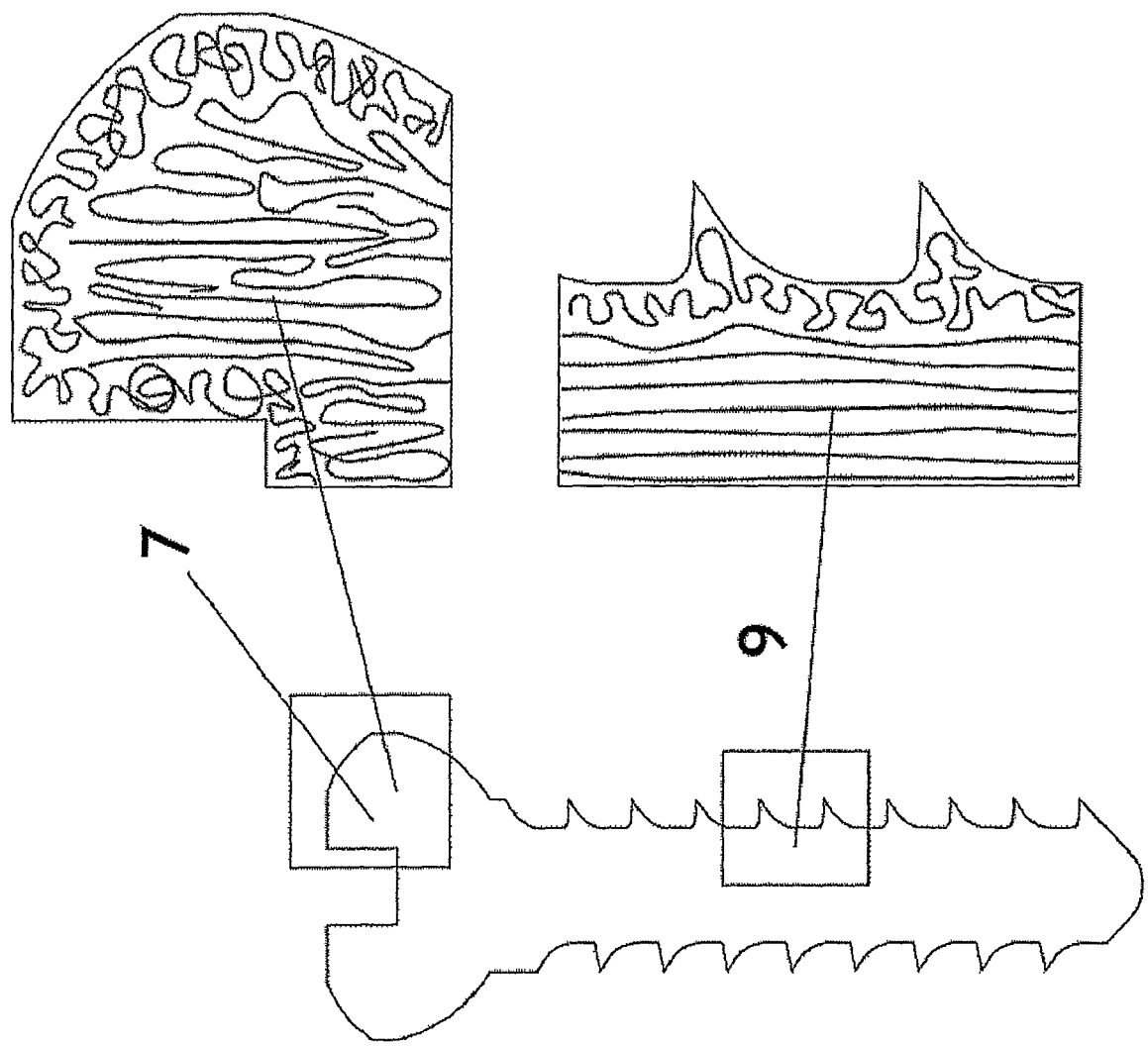
FIG. 4 a screw forged with a forming device according to FIG. 3 and two enlarged cutouts showing the polymer chain orientation of the screw head and the shaft of the screw.

In FIGS. 1 to 3 various types of arrangements of forming and forging devices are represented allowing preparation of highly oriented implantable polymeric medical devices with simple and complex shapes.

In FIG. 1 the forming device 1 is realized through an extrusion die 20 which has a through hole 11 with a longitudinal axis 12 and orthogonal to this longitudinal axis 12 a circular or rectangular cross-section in order to produce monofilaments, ribbons or bars 2 with circular or rectangular cross-sections. The through hole 11 is provided with a conical section 13 tapering towards the outlet 15 of the extrusion die 20. The monofilaments, ribbons or bars are produced by pushing or pulling a longitudinal rod 2 through the extrusion die 20 parallel to the longitudinal axis 12 from the inlet 14 to the outlet 15 whereupon the longitudinal rod 2 is radially compressed when passing through the conical section 13 within the through hole 11.

In FIG. 2 the forming device 1 comprises an extrusion die 20 being provided with a through hole 11 having an annular configuration allowing the preparation of tubular objects 3. The extrusion die 20 is therefore provided with an insert 16 which has cone 17 or pyramid to narrow the annular slot 18 between the inlet 14 and the outlet 15 of the extrusion die 20.

Upon pushing or pulling the raw tubular object through the extrusion die 20 between the inlet 14 and the outlet 15 the wall of the tubular object 3 is radially compressed by widening the aperture of the tubular object 3.

In FIG. 3 a forming device 1 is shown allowing preparation of individual polymeric objects with complex shapes, e.g. bioresorbable screws by forging of high-strength, high modulus elements produced using the pulling/pushing process of the invention. A section of the bar 10 with a predetermined length is swollen in an adequate additive and placed in the opened position of the forming device 1 (FIG. 3a). The forming device 1 comprises a forging die 21 being separated in the direction of the central axis 19 of the bar 10. The two parts of the forging die 21 have symmetrical compression moulds 22 whereby a first section 23 is provided with a negative screw thread 24 and a second section 25 is provided with a negative of the lower part of a screw head 7. Next, the compression moulds 22 of the forming device 1 are closed (FIG. 3b), and the piston 4 with one end preshaped to form the screw head 7 (e.g. Philips, socket pin head) is coaxially pressed down in the forming device 1, to plastically deform one end of the bar 10 into the head 7 of the screw 8.

In FIG. 4 the polymer chain orientation in the screw 8 produced by forging of high-strength, high modulus elements produced using the pulling/pushing process of the invention is depicted. The polymer chains in the screw core 9 are highly oriented, while the polymer chains at the screw's surface layer are folded. The polymer chain orientation in the screw head 7 decreases gradually from the center towards the surface.

The following are typical examples for the preparation of resorbable or degradable polymeric medical objects according to the invention:

EXAMPLE 1

Poly(L-lactide) with a viscosity-average molecular weight of 400.000 dalton was used for the preparation of resorbable monofilaments. Monofilaments were produced by extrusion of 30 wt.-% polymer solution in chloroform/methyl acetate mixture at room temperature through a nozzle with I.D. of 2 mm. After evaporation of liquids from the polymer, the as-extruded fiber had a diameter of 2.1 mm, an ultimate tensile strength of 15 MPa and a Young's modulus of 3 GPa. The dry fiber was next swollen in ethanol-methylacetate mixture and pulled at temperature of 80° C. via the conical forming device with an inner diameter of 0.4 mm. Tensile strength of the oriented fiber was enhanced to 600 MPa and the Young's modulus to 8 GPa.

EXAMPLE 2

Poly(L-lactide) a with viscosity-average molecular weight of 700.000 dalton was melt-extruded into a cylindrical bar with a diameter of 8 mm having a tensile strength of 60 MPa and a Young's modulus of 4 GPa. The bar was cut to 10 cm pieces and then exposed to the action of methylpyrrolidone/methyl acetate/ethanol mixture for 5 hours. The swollen pieces of the bar were placed in a piston-cylinder forming device heated to 70° C. and pushed through an outlet with a diameter of 4 mm into a chamber maintained under vacuum. This allowed for removal of liquid residues. The resulting polymeric pins had a tensile strength of 320 MPa and the Young's modulus of 7 GPa.

EXAMPLE 3

A poly(L-lactide) bar 5×10 mm having a tensile strength of 80 MPa and Young's modulus of 4 GPa, was swollen in dimethylsulfoxide/ethanol mixture and subsequently pulled at 70° C. through a forming device with a rectangular cross-section into a ribbon of 2×6 mm. The resulting ribbon after removal of the swelling agent had a tensile strength of 360 MPa and a Young Modulus of 7 GPa. The ribbon was cut into length of 38 mm to be used as maxillofacial bone plates. These were drilled with a borer to accommodate resorbable screws with the diameter of 2.0 mm.

EXAMPLE 4

Poly(L-lactide) with a viscosity-average molecular weight of 360.000 dalton was dissolved in chloroform to produce a polymer solution with concentration of 3.5% wt-%. Crystalline hydroxyethylcellulose (0.25 wt-%) was added upon vigorous stirring to polylactide solution to produce a mixture containing 2.0% of hydroxyethylcellulose and 98% of polylactide.

Chloroform was partially evaporated from the mixture to obtain final concentration of both polymers in solution of 12.5 wt-%. This solution was extruded at 25° C. to produce a monofilament with diameter of 1.2 mm.

This monofilament was pulled next at 90° C. through a forming device with diameter of 0.6 mm leading to the monofilament with an ultimate tensile strength of 210 MPa and Young's modulus of 6 GPa, as compared with 50 MPa and 3 GPa respectively, for as-extruded monofilament.

EXAMPLE 5

Poly(L/DL-lactide) with a viscosity-average molecular weight of 300.000 dalton was dissolved in chloroform to produce a polymer solution with concentration of 3.5% wt-%. Thermotropic hydroxyethyl cellulose acetate (0.3 wt-%) was added upon vigorous stirring to polylactide solution to produce a blend containing 2.0% of hydroxyethylcellulose and 98% of polylactide.

Chloroform was partially evaporated from the mixture to obtain final concentration of both polymers in solution of 14.0 wt-%. The solution was extruded at 25° C. to produce a monofilament with diameter of 1.5 mm.

This monofilament was pulled next at 80° C. through a forming device with diameter of 0.6 mm leading to the monofilament with an ultimate tensile strength of 210 MPa and Young's modulus of 6 GPa, as compared with 50 MPa and 3 GPa respectively, for as-extruded monofilament.

EXAMPLE 6

Poly(L/DL-lactide) 80/20% with a viscosity-average molecular weight of 260.000 dalton was dissolved in acetone-dioxane mixture to produce a polymer solution with concentration of 3.5% wt-%. Thermotropic poly(β-benzyl-L-glutamate) was dissolved in dimethyl formamide (0.2 wt-%) and was added upon vigorous stirring to polylactide solution to produce a mixture containing 0.1% of poly(β-benzyl-L-glutamate) and 99.9% of polylactide.

After solvent evaporation the foil was cut to pieces and melt-extruded to produce a monofilament with diameter of 1.4 mm.

This monofilament was pulled next at 90° C. through a forming device with diameter of 0.6 mm leading to the monofilament with an ultimate tensile strength of 350 MPa and Young's modulus of 7 GPa, as compared with 30 MPa and 3 GPa respectively, for as-extruded monofilament.

EXAMPLE 7

Poly(L/DL-lactide) 80/20% with a viscosity-average molecular weight of 260.000 dalton was dissolved in acetone: dioxane 1:2 mixture to produce a polymer solution with concentration of 4.0 wt-%. Crystalline hydroxyethylcellulose was dissolved in water (0.1 wt-%) and added upon vigorous stirring to polylactide solution to produce a mixture containing 99.9% of polylactide and 0.1 wt-% of hydroxyethylcellulose. After solvent evaporation the resulting film was cut to chips and extruded from the melt to produce a monofilament with diameter of 1.2 mm.

This monofilament was pulled next at 90° C. through a forming device with diameter of 0.6 mm leading to the monofilament with an ultimate tensile strength of 220 MPa and Young's modulus of 7 GPa, as compared with 50 MPa and 4 GPa respectively, for as-extruded monofilament.

EXAMPLE 8

Poly(L/DL-lactide) 80/20% with a viscosity-average molecular weight of 400.000 dalton was melt-extruded into bars with circular cross-sections with a diameter of 5 mm. The monofilament was swollen in liquid crystalline solvents. The LC solvents used were 4-octyl-4-biphenyl carbonitrile, 4-(trans-4-pentyl-cyclohexyl) and 4-4'-diheptyl azoxybenzene mixed with ethanol or n-hexane. The monofilament was kept in the liquids until its weight increased due to swelling by 0.1 to 1%. Next the monofilament was pulled at 60° C. through the nozzle with a diameter of 2.5 mm. The oriented polymeric object had the tensile strength of 210 MPa and the tensile modulus of 8000 MPa.

The invention claimed is:

1. A method for producing a resorbable or degradable polymeric medical device, comprising
   treating a solid polymeric object with an additive, said additive comprising a biocompatible liquid-crystalline solid or fluid compound, wherein said additive is present in an amount of 0.005 to 20% of the dry weight of said polymeric object and after being absorbed by said polymeric object, does not dissolve more than 0.01 to 1% of the total mass of said polymeric object;
   applying compressive forces to said polymeric object at a minimum temperature $T_{min}=T_g-50°$ C., $T_g$ being the glass transition temperature of the polymer the said polymeric object is made of, and at a maximum temperature $T_{max}T_m-5°$ C., $T_m$ being the melting peak temperature of the polymer the said polymeric object is made of.

2. The method of claim 1, wherein said compressive forces are produced by the pushing or pulling of said solid polymeric object via a guiding device with an inlet and an outlet, the cross-section of the inlet being larger than the cross-section of the outlet.

3. The method of claim 1, wherein said additive comprises aliphatic mono-, di- or trialcohols, chlorinated solvents, aliphatic acetates, aliphatic aldehydes and ketones, aliphatic carboxylic acids and lactones, carboxylic esters, alkenic acetates, alkenic methyl esters, acetylenic alcohols, acetylenic acids and esters, monocarbocyclic carboxylic acids and lactones, monocarbocyclic esters, esters of hydroxy acids, or dibasic aliphatic acids.

4. The method of claim 1, wherein said additive comprises ethyl alcohol, methyl alcohol, isopropyl alcohol, ethylene diol, diethylene diol, propylene diol, L-alaninol, D-alaninol, acetone, tetrahydrofuran, methyl acetate, ethyl acetate, methyl lactate, ethyl lactate, isopropyl lactate, 2-methylbutanol, 4-methylhexanol, 2-methylbutanal, 3-methylpentanal, 4-methylhexanal, methyl-2-methylbutanoate, ethyl-3-methyl-2-oxo-pentanoate, 2-pentyl acetate, 2-hexyl acetate, 2,5,6-trimethyl-2-heptanol, chloroform, methylene chloride, trifluoroethanol, dioxane, 2-ethyl-1-hexanol acetate, 2-ethyl-1-hexyl acetate, 2-ethylhexanyl acetate, 2-ethylhexyl ethanoate, acetic acid, 2-ethylhexyl ester, beta-ethylhexyl acetate, ethylhexyl acetate, octyl acetate, alpha-ethylhexyl ester, or a mixture thereof in various proportions.

5. The method of claim 1, wherein said additive is present in an amount of 0.01 to 5.00% of the dry weight of said polymeric object.

6. The method of claim 1, wherein said additive is present in an amount of 1 to 2% of the dry weight of said polymeric object.

7. The method of claim 2, wherein said pushing or pulling is performed at a minimum temperature $T_{min}=T_g+10°$ C.$<T_{min}<T_m-10°$ C.

8. The method of claim 1, wherein said pushing or pulling is performed at a maximum temperature $T_{max}=T_g$.

9. The method of claim 2, wherein said polymeric object, during pushing or pulling, is in direct contact with the walls of said forming device.

10. The method of claim 2, wherein said pushing or pulling is performed in such a way that the walls at or near the opening of said forming device are contacted only indirectly by the polymeric object via an intermediate layer of said additive, wherein said intermediate layer is squeezed out from the polymeric object upon being passed through said forming device.

11. The method of claim 1, wherein said polymeric object has a molecular weight in the range of 30,000 to 1 million daltons.

12. The method of claim 11, wherein said polymeric object has a molecular weight in the range of 50,000 to 500,000 daltons, or in the range of 200,000 to 400,000 daltons.

13. The method of claim 1, wherein said polymeric object has a polydispersity or molecular weight distribution $M_w/M_n$ in the range of 1 to 100, or in the range of 1.1 to 3.0.

14. The method of claim 1, wherein said polymeric object comprises poly(L-lactide), poly(DL-lactide), copolymers of L-lactide with D-lactide and/or DL-lactide, copolymers of lactides with caprolactone, glycolide, trimethylene carbonate, caprolactam, aminoacids, ethylene oxide diols, terpolymers of lactides with glycolide and caprolactone, polyglycolide, polycaprolactone, polyglycolide-co-trimethylene carbonate, polydioxanone, polyesteramides, polyurethanes, polyhydroxybutyrate, or poly(hydroxybutyrate-co-hydroxyvalerate).

15. The method of claim 1, wherein said liquid-crystalline solid compound comprises p-hydroxybenzoic acid, 2-decanyloxy-4-hydroxybenzoic acid, cinnamate compounds, hydroxyethylcellulose, hydroxypropylcellulose, hydroxyethyl cellulose acetate, poly(γ-benzyl-L-glutamate), poly(ε-carbobenzoxy-L-lysine-co-decenyl-glutamate), or a mixture thereof in various proportions.

16. The method of claim 1, wherein said liquid-crystalline fluid compound comprises n-butyl stearate, [p-(n-decyloxy-benzylidene)-p-amino-(2-methyl-butyl)]cinnamate, phenylpropyl cinnamate, alkyl lactate, ethanol-n-alkyl propionate, mixtures of cholesteryl chloride/cholesteryl nonanoate, trans, trans-4'-n-butylbicyclo-hexane-4-carbonitrile, or a mixture thereof in various proportions.

17. The method of claim 1, wherein the ratio between the initial cross-section of said polymeric object and the final cross-section of said polymeric object after being passed through said forming device is in the range of 1.1 to 100, 1.1 to 20, or at least 2.

18. The method of claim 1, wherein the rate at which the polymeric object is pushed or pulled through said forming device is in the range of 0.1 to 100,000 mm/min.

19. A resorbable or degradable polymeric medical device manufactured by the method of claim 1, wherein said device has a tensile strength in the range of 100 to 5,000 MPa and a tensile Young's modulus in the range of 4,000 to 30,000 MPa.

* * * * *